United States Patent [19]
Klaus

[11] Patent Number: 6,165,983
[45] Date of Patent: *Dec. 26, 2000

[54] USE OF COLLAGEN FOR THE TREATMENT OF DEGENERATIVE ARTICULAR PROCESSES

[76] Inventor: Edwin Klaus, Juliuspromendade 7, 8700 Wuerzburg, Germany

[*] Notice: This patent is subject to a terminal disclaimer.

[21] Appl. No.: 09/401,377

[22] Filed: Sep. 22, 1999

Related U.S. Application Data

[63] Continuation of application No. 08/050,184, filed as application No. PCT/DE92/00629, Jul. 28, 1992, Pat. No. 6,083,918.

[30] Foreign Application Priority Data

Jul. 31, 1991 [DE] Germany .............................. 41 25 400

[51] Int. Cl.⁷ .................................................. A61K 38/39
[52] U.S. Cl. ................................ 514/21; 514/14; 530/356
[58] Field of Search ............................ 530/356; 514/14, 514/21

[56] References Cited

U.S. PATENT DOCUMENTS

| | | |
|---|---|---|
| 3,683,076 | 8/1972 | Rovati . |
| 3,966,908 | 6/1976 | Balassa . |
| 4,424,208 | 1/1984 | Wallace et al. .......................... 424/177 |
| 4,473,551 | 9/1984 | Schinitsky . |
| 4,582,640 | 4/1986 | Smestad et al. . |
| 4,704,273 | 11/1987 | McMichael . |
| 4,804,745 | 2/1989 | Koepff et al. . |
| 4,883,864 | 11/1989 | Scholz ...................................... 530/356 |
| 5,002,071 | 3/1991 | Harrell . |
| 5,035,056 | 7/1991 | Kludas . |
| 5,137,875 | 8/1992 | Tsunenaga et al. . |
| 5,206,023 | 4/1993 | Hunziker ................................ 424/423 |
| 5,639,796 | 6/1997 | Lee . |

FOREIGN PATENT DOCUMENTS

| | | |
|---|---|---|
| 0 701 570 | 1/1968 | Belgium . |
| 0 254 289 | 7/1986 | European Pat. Off. . |
| 0 254 289 | 7/1987 | European Pat. Off. . |
| 0 338 813 | 10/1989 | European Pat. Off. . |
| 2 613 620 | 4/1987 | France . |
| 2 405 002 | 2/1974 | Germany . |
| 2 462 222 | 2/1974 | Germany . |
| 59-067218 | 4/1984 | Japan . |
| 62-070318 | 3/1987 | Japan . |
| 0 494 250 | 7/1968 | Switzerland . |
| WO 92/06708 | 4/1992 | WIPO . |

OTHER PUBLICATIONS

Buvardi ed. (1989). *The Merck Index*. Merck & Co. Inc.: Rathway, NJ., p. 4353.

Carron. (1978). "Relieving pain with nerve blocks," *Geriatrics* 33(4):49–57.

Hernandez et al. (1988). "The immune response of guinea-pigs to type II collagen: poor cross-reactivity with homologous type II collagen accounts for resistance to collagen-induced arthritis," *Immunol.* 63:619–624.

Moya (1981). "Treatment of osteoarthritis of the spine and herpetic neuralgia at the Pain Center, Mount Sinai Medical Center," *NIDA Res. Monogr. Ser.* 36:118–121.

Myers et al. (1989). "A CD4 cell is capable of transferring suppression of collagen-induced arthritis," *J. Immunol.* 143(2):3976–3980.

*Stedman's Medical Dictionary*. (1982). 24th Edition, Williams & Wilkins: Baltimore, MD., p. 271.

Steffen et al. (1975). "Collagen-induced acute synovitis in collagen-immunized rabbits," *Z Immunitatsforsch Exp Klin Immunol.* 150(3):432–446.

Steffen et al. (1978). "Acute autoimmune collagen-induced arthritis in rabbits," *Z. Rheumatol.* 37:275–285.

Thorp et al. (1992). "Type II collagen-immune complex arthritis in sheep: collagen antibodies in serum, synovial fluid and afferent lymph," *Clin. Exp. Rheumatol.* 10:143–150.

Trentham et al. (1977). "Autoimmunity to type II collagen an experimental model of arthritis," *J. Exp. Med.* 146:857–867.

Volodina et al. (1991). "Collagen of human cartilage in deforming arthrosis," *Ukr. Biokhim Zhurn.* 63(4):47–51 (English translation attached).

*Primary Examiner*—Chhaya D. Sayala
*Attorney, Agent, or Firm*—Morrison & Foerster LLP

[57] ABSTRACT

The invention relates to the use of collagen for the production of a drug for the treatment of degenerative articular processes. An injection suspension is preferably produced, which contains collagen and possibly a local anaesthetic. This injection suspension is applied into the affected joints by means of an injection.

20 Claims, No Drawings

USE OF COLLAGEN FOR THE TREATMENT OF DEGENERATIVE ARTICULAR PROCESSES

This application is a continuation of U.S. patent application Ser. No. 08/050,184, filed May 3, 1993 now U.S. Pat. No. 6,083,918, which is a 371 of PCT Application Serial No. PCT/DE92/00629, Jul. 28, 1992, which claims priority to German Patent Application No. P41524007, filed Jul. 31, 1991.

The invention relates to the use of collagen for the treatment of degenerative articular processes.

The basic type of degenerative, non-inflammatory joint diseases is arthropathy or Arthrosis deformans in old age. Squat-bodied human beings, more men than women, after the 50th year are mainly affected. The condition begins slowly, but also progresses intermittently and at the beginning without pain. The joints are only tender upon certain movements. Avoiding strain on the joints promotes the progression of the condition, but exercise and massages afford relief. Good successes can also be achieved by the treatment with ultra-short waves.

Further therapies, which have been customary so far, are the systematic administration of non-steroidal antirheumatic agents and possibly intra-articular injections of agents for the protection of cartilage, homoeopathic agents, local anaesthetics or cortisone. However, these therapies have the disadvantage that the destruction of the joints occurring finally due to degenerative joint processes cannot be prevented, but only delayed, since the new formation of synovial fluids, such as mucopolysaccharides, cannot be stimulated, and no synovial fluid is introduced into the affected joint from the outside.

Reconstituted type II collagen can be used for the detection of antibodies against intact type II collagen in the blood in the case of arthrorheumatism (JP-A 62-012 800).

Collagens are long-fibred, linear-colloid, highly molecular scleroproteins of the extracellular matrix, which are found in connective tissues (e.g. skin, cartilage, sinews, ligaments and blood vessels), in the protein-containing ground substance of the bone (ossein) and in dentin together with proteoglycans. With a share of 25 to 30% they are considered to be the quantitatively most frequent animal proteins. The structural basic unit of collagen, the tropocollagen (MW approx. 300,000), consists of three polypeptide chains in the form of special left-wound helices which, in turn, are righthandedly twisted around one other according to the technique known in ropery (triple helix). The tropocollagen molecule is a "rope" with a length of 280 nm and a diameter of 1.4 nm; the fibrils have a cross-section of 200 to 500 nm (see Römpps Chemielexikon, vol. 3, page 2297, 1990).

As opposed to most proteins of the animal body, the collagens are not continuously renewed. Once they are formed, they do not participate in the metabolism any more and age due to regular increase in cross-linking due to the formation of hydrogen bridge bonds, ester bonds of amino acid residues with sugar residues and of isopeptide bonds between long-chain amino acid chains.

Modified collagen is used in medicine as a temporary skin replacement, as a replacement for cornea and vitreous humour of the eye, as a replacement for sinews, synovial sheaths, hollow organs and blood vessels, as a blood plasma substitute and in wound healing (EP-B 52288, JP-A-52-076 416). Collagen sponge is i.a. used as a haematostatic. Collagen containing drugs are used to improve dilatatable deformations of the skin as they occur in scars, in skin atrophy caused by various causes and in skin creases caused by age. These collagen-containing drugs are injected under the skin areas to be filled and, for this reason, contain, as a rule, a local anaesthetic.

It is the object of the present invention to produce a drug for the therapy of degenerative articular processes which does not have the aforementioned disadvantages.

This object is attained according to the invention by using collagen for producing a drug for the treatment of degenerative articular processes.

The used collagen is unsoluble collagen, which can e.g. be obtained from calf and bovine skin; however, collagen from bovine skin is preferred.

The collagen is preferably contained in an injection suspension, particularly preferred in an amount of about 20 to 50 mg/ml. The injection suspension is applied by means of injection into the joints according to the invention in the case of degenerative articular diseases such as arthrosis or activated arthrosis. For this reason, a local anaesthetic such as bupivacaine or lidocaine is preferably contained. Lidocaine is contained with particular preference. The preferred amount of the contained local anaesthetic is 1 to 5 mg/ml.

As opposed to former therapies, the intraarticular use of collagen according to the invention in a drug has the advantage that it promotes the lubrication process which only takes place insufficiently in an arthrosis due to its properties, without attacking any substances, i.e without causing a damage.

"Carrier substances", e.g. agents for the protection of cartilage can be included in the collagen as a secondary element.

Examples of such agents for the protection of cartilage are the preparations Dona 200 (active substance: D-glucosamine) and Dona 22S (active substance: D-glucosamine sulfate) and the homoeopathic agents Zeel and Heel.

The homoeopathic agent has the following composition: 2.2 ml contain: extract (1:10) from *Cartilago suis* 22 ng, extract (1:10) from *Funiculus umbilicalis suis* 22 ng, extract (1:10) from *Embryo suis* 22 ng, extract (1:10) from *Placenta suis* (hormone-free) 22 ng, Rhus toxicodendr. $\phi$ 0.2 mg, arnica $\phi$ 0.2 mg, Dulcamara $\phi$0.22 $\mu$g, Symphytum $\phi$ 22 $\mu$g, Sanguinaria $\phi$ 33 $\mu$g, sulphur $\phi$ 39.6 $\mu$g, Nacid 0.22 ng, coenzyme A 0.22 ng, ($\pm$)-a-liponic acid, 0.22 ng, sodium oxalic acetat 0.22 ng. Moreover, the drug can still be slightly tinted, e.g. with compatible dyes.

The following examples explain the invention.

EXAMPLES 1 TO 5

Various compositions of the active substance combination in the injection suspension are indicated in the following examples.

1 ml of injection suspension containing:

1.
   20 mg of collagen from calf skin
   2 mg bupivacaine;
2.
   30 mg of collagen from bovine skin
   2 mg of bupivacaine;
3.
   35 mg of collagen from bovine skin
   3 mg of lidocaine;
4.
   40 mg of collagen from bovine skin
   3 mg of lidocaine;

5.
   50 mg of collagen from calf skin
   3.5 mg of bupivacaine.

Application Example 1

A young women, 32 years old, with therapy-resistant gonalgia, was treated about 1½ years ago with injections of 0.5 ml of the collagen-containing injection suspension according to example 3 intraarticularily into the joints on the one side and 1.0 ml on the other side; subsequently she was completely symptom-free. It was not necessary to repeat the treatment.

Application Example 2

Injections in the case of an extension of the hip joint resulted in an improvement following prior injection of 2 ml of local anaesthetic only for the purpose of the correct needle position, after 2 ml of the collagen injection suspension according to example 5 had been infiltrated intraarticularly into each joint side. The observation time was approximately two years. It was found that, above all, the initial, primary arthrotic complaints had come to a complete standstill after 6 months.

Further similar case reports are available.

Application Example 3

Intraarticular injections of 1 ml of the collagen-containing injection suspension according to example 3 brought about an approx. 70% improvement of the complaints according to the patient's statement in the case of a left-side severe gonarthrosis. Since about 2 years, the complaints have remained constant.

What is claimed is:

1. A method for treating arthropathies, comprising:
   administering an intraarticular injection of collagen to a human patient having an arthropathy, wherein said intraarticular injection results in elimination of arthropathy symptoms for at least 6 months.

2. The method of claim 1 wherein said composition further comprises a chondroprotective agent.

3. The method of claim 2 wherein said chondroprotective agent is D-glucosamine.

4. The method of claim 2 wherein said chondroprotective agent is D-glucosamine sulfate.

5. The method of claim 1 wherein said composition contains about 20 to 50 mg/ml collagen.

6. The method of claim 1 wherein said collagen is from bovine skin.

7. The method of claim 1 wherein said composition further comprises a local anesthetic.

8. The method of claim 5 wherein local anesthetic is about 1 to 5 mg/ml.

9. The method claim 1, wherein said intraarticular injection is into said subject's knee.

10. The method claim 1, wherein said intraarticular injection is into said subject's hip.

11. A method for treating arthropathies, comprising:
    administering an intraarticular injection of a composition consisting essentially of collagen to a human patient having an arthropathy, wherein said intraarticular injection results in elimination of arthropathy symptoms in at least 6 months.

12. The method of claim 10 wherein the composition further consists essentially of a chondroprotective agent.

13. The method of claim 11 wherein the chondroprotective agent is D-glucosamine.

14. The method of claim 11 wherein the chondroprotective agent is D-glucosamine sulfate.

15. The method of claim 10 wherein said composition consists essentially of 20 to 50 mg/ml collagen.

16. The method of claim 10 wherein said collagen is from bovine skin.

17. The method of claim 10 wherein said composition further consists essentially of a local anesthetic.

18. The method of claim 16 wherein said local anesthetic is about 1 to 5 mg/ml.

19. The method claim 10, wherein said intraarticular injection is into said subject's knee.

20. The method claim 10, wherein said intraarticular injection is into said subject's hip.

\* \* \* \* \*

UNITED STATES PATENT AND TRADEMARK OFFICE

CERTIFICATE OF CORRECTION

PATENT NO. : 6,165,983

DATED : December 26, 2000

INVENTOR(S) : Edwin KLAUS

It is certified that error appears in the above-identified patent and that said Letters Patent is hereby corrected as shown below:

ON THE TITLE PAGE

Under [76] Inventor section, replace "Juliuspromendade" with --Juliuspromenade.

Signed and Sealed this

Twenty-ninth Day of May, 2001

Attest:

NICHOLAS P. GODICI

Attesting Officer

Acting Director of the United States Patent and Trademark Office